US006536938B2

(12) United States Patent
Zhou

(10) Patent No.: US 6,536,938 B2
(45) Date of Patent: Mar. 25, 2003

(54) MICROORGANISM CULTURE APPARATUS AND METHOD AND MICROORGANISM CULTURE SYSTEM USING SUCH APPARATUS

(76) Inventor: Lei Zhou, 12 East Road Qianfoshan, Jinan, Shangdong Province 250014 (CN)

( * ) Notice: Subject to any disclaimer, the term of this patent is extended or adjusted under 35 U.S.C. 154(b) by 0 days.

(21) Appl. No.: 09/737,944

(22) Filed: Dec. 18, 2000

(65) Prior Publication Data

US 2001/0043508 A1 Nov. 22, 2001

(30) Foreign Application Priority Data

May 18, 2000 (CN) ........................................ 00117635 A

(51) Int. Cl.[7] ................................................ B01F 13/08
(52) U.S. Cl. .......................... 366/273; 366/601; 261/87
(58) Field of Search ................................ 366/102, 145, 366/249–251, 253, 273, 274, 348, 601; 416/3; 261/87; 435/302.1; 266/234

(56) References Cited

U.S. PATENT DOCUMENTS 3,607,659 A * 9/1971 Bloomer
3,622,129 A * 11/1971 Mazowski
4,162,855 A * 7/1979 Bender
4,204,774 A * 5/1980 De Bruyne
4,382,685 A * 5/1983 Pearson
4,498,785 A * 2/1985 De Bruyne
4,596,779 A * 6/1986 Ono
4,649,118 A * 3/1987 Anderson
4,760,028 A * 7/1988 De Bruyne et al.
5,267,791 A * 12/1993 Christian et al.
5,470,152 A 11/1995 Rains
5,529,391 A * 6/1996 Kindman et al.
5,577,837 A * 11/1996 Martin et al.
6,193,410 B1 * 2/2001 Puckett, II

FOREIGN PATENT DOCUMENTS

| | | | |
|---|---|---|---|
| GB | 2178971 | * | 2/1987 |
| JP | 61-67475 | * | 4/1986 |
| JP | 64-56127 | * | 3/1989 |
| JP | 6-261747 | | 9/1994 |
| RU | 808114 | | 8/1976 |
| WO | 93/21301 | * | 10/1993 |

* cited by examiner

*Primary Examiner*—Charles E. Cooley
(74) *Attorney, Agent, or Firm*—Burns, Doane, Swecker & Mathis, L.L.P.

(57) ABSTRACT

This invention is a magnetically coupled microorganism culture apparatus used in the expansion culture of microorganisms, especially in the expansion culture conducted for test tube microorganisms. In one example, the culture apparatus is powered by a micro motor, rotation of the micro motor is transferred to the air impeller by virtue of a magnetically coupled device, causing the air impeller to rotate at a high speed. Under the effect of centrifugal force, the air in the air impeller is sprayed into the culture medium liquid in the container for the growth of microorganisms. This invention is substantially different from the shaker being used today, thus achieving the purpose of reducing cost and saving energy.

11 Claims, 6 Drawing Sheets

MICROORGANISM CULTURE APPARATUS AND METHOD AND MICROORGANISM CULTURE SYSTEM USING SUCH APPARATUS

BACKGROUND OF THE INVENTION

1. Field of the Invention

This invention relates to a microorganism culture apparatus, more particularly to the microorganism culture apparatus and method for conducting air exchange between inside and outside of the container in an aseptic environment. This invention is useful in the expansion culture of microorganisms, especially in the expansion culture conducted for test tube microorganisms.

2. Description of the Related Art

For the microorganism culture and especially the expansion culture conducted for test tube microorganisms, mechanical shakers are widely used. Currently, shakers in use domestically and abroad vary in model and type, including DXY single-shaft rotary shaker and CXY-2 reciprocating shaker (designed and supervised by Shanghai Industrial Microbiology Institute and manufactured by Chaoqiao Light Industry Machinery Factory in Wuxi Jiangsu); Model 4520 shaker produced by Forma Scientific Co. USA. Whichever model it is, the operation procedure is basically the same: place on an operation table multiple glass flasks that contains liquid culture medium already vaccinated, turn on the power, and let the shaker shake in a certain vibration frequency till the end of the microorganism growth period. Therefore, the main working principle involved is to enable the vibration of the liquid surface of the culture medium, allowing the air to enter into the flasks and provide for the microorganism growth. However, due to such a working principle, some disadvantages prevail in current shakers, regardless of the original producer:

1) Because the entire operation desk shakes, energy consumption is generally big, about 1 KVA for the entire machine;
2) Long-time mechanical vibration is inclined to cause mechanical failure;
3) Long-time mechanical abrasion generates noise and pollutes the environment;
4) Shaking rate limits the liquid allowed in the flask, usually covering only 20% of the total volume;
5) Composition variability is poor. Even when an experiment requires only one or two flasks of microorganism, the entire machine shall be operated, thus wasting energy;
6) Mechanical maintenance is difficult.

An USSR patent No. SU-808114 issued on Aug. 2, 1976 discloses a mixer for mixing solids and gases in culture liquids. However, this document does not mention how the air exchange is proceeded between the mixer and the outside environment.

A Japanese patent published on Sep. 20, 1994 (Publication No.6-261747) discloses a liquid culture apparatus and method that utilizes electro-magnetic agitation. In this application, a winged magnetic impeller flows on the free surface of the culture liquid in the container by virtue of buoyant force. The impeller is driven to rotate through the rotation of an external magnetic force at the bottom of the container. As a result, circulation of the culture liquid in the container is achieved, resulting in normal culture of biological cells. Nevertheless, no details concerning air exchange are discussed in this publication.

A U.S. Pat. No. 5,470,152 issued on Nov. 28, 1995 discloses an agitation tank characterized by a magnetically coupled mixer. The mixer includes a drive magnet that is connected to an electric motor and a driven magnet whose lower portion is fastened to an impeller. Both magnets are magnetically coupled so that one cycle of rotation in the drive magnet results in exactly one cycle of rotation in the driven magnet and the impeller. The drive magnet is driven to rotate by the electric motor, resulting ultimately in the rotation of the impeller and the circulation of the culture liquid in the tank. However, this patent does not mention the path for controlling the input and output of air, especially hydrogen.

Considering these, the objective of this invention is to provide an air exchanger inserting into the container, thus achieving an aseptic air exchange between inside and outside of the container in a more energy-efficient way.

SUMMARY OF THE INVENTION

The first aspect of this invention provides a magnetically coupled microorganism culture apparatus which includes: a container for holding microorganism culture medium liquid, said container having one or a plurality of gas outlets (8) and an opening (21) at its top, each said outlet having an air filtering film; a sealed filtering cap fastened at the top the container and covering said opening (21), the sealed cap having an inlet which is covered by an air filtering film; a hollow air sucker in the sealed cap, which is rotatable relative to the sealed cap and the flask, passing downward through said opening and then entering into the container; a hollow air impeller fastened to lower end of the sucker, being in a gaseous communication with the sucker; a driven magnet fastened to upper end of the sucker; a resisting structure fastened to the container near the impeller, for preventing the liquid in the container from generating eddy flow; wherein when said apparatus is applied to rotary magnetic field, the driven magnet brings the sucker and impeller to rotate along with it, thus sucking filtered air which enters into the sucker via the inlet into the liquid by centrifugal force so as to achieve the objective of air exchange.

The second aspect of this invention is to provide a microorganism culture apparatus, which includes: a container for holding culture medium liquid, having one or a plurality of gas outlets and an opening at its top, each said outlet being covered by an air filtering film; an air-purifying chamber, on the wall of which are one or a plurality of inlets covered by air filtering films; a hollow air sucker in the air-purifying chamber, entering the container through the opening, upper end of the sucker being fastened to the drive shaft of a micro motor via a coupling, the sucker having an air filtering film at its upper opening; a hollow air impeller fastened to the lower end of the sucker, said impeller being in a gaseous communication with said sucker; a resisting structure fastened to the container near the impeller, for preventing the liquid in the container from generating eddy flow; other than the gas sucker, there is almost no path to the container from the air-purifying chamber; when the micro motor is on, it drives the sucker and impeller to rotate, thus, sucking the filtered air which enters into the sucker via the inlet into the liquid by the centrifugal force and achieving the goal of air exchange between the inside and outside of the container.

The third aspect of this invention is to provide a method for conducting aseptic air exchange for the microorganism in a container by using magnetically coupled rotary means, said container including a container body for holding microorganism culture medium liquid, the container body comprising: one or a plurality of outlets (8) and an opening (21) at its top, each said outlet being covered by an air filtering film; a resisting structure located at the bottom of and fixed relative to the container for preventing the liquid in the container from generating eddy flow; said magnetically coupled rotary means comprising: a sealed filtering cap, on said cap is disposed with an inlet covered by an air filtering film; a hollow sucker placed through the sealed cap and being rotatable relative to the sealed cap; an impeller fixed at the lower end of the sucker, said impeller being in a gaseous communication with the sucker; a driven magnet fastened to the upper end of the sucker; said method including the following steps: lowering the sucker together with the impeller through the sealed cap into the container so that the impeller is at the same level as said resisting structure; fastening the filtering sealed cap onto the container opening, so that air flow between the sealed cap and the container is only allowed through the sucker; applying rotary magnetic field to the driven magnet; the driven magnet bringing the sucker and further the impeller to rotate; the filtered air which enters into the sucker via the inlet is sucked into the liquid by the centrifugal force so as to achieve an air exchange.

The fourth aspect of this invention is to provide a microorganism culture system using the above culture apparatus, which includes a box body, an adjustable DC power, a plurality of microorganism culture apparatuses placed in the box body and a corresponding number of time relays, wherein each culture apparatus is one according to the first or second aspect of this invention respectively; said plurality of culture apparatuses are divided into said number of groups, with the micro motors of each group are controlled by time relays with different duty cycles so that different amount of oxygen may be delivered to different groups of culture apparatuses, thereby achieving the object of cultivating different microorganisms in one box at the same time.

This invention is different from various currently used shakers in working principle. It has following advantages: (1) saving energy; (2) being free of mechanical vibration so that mechanical fault and noise are greatly decreased; (3) the amount of filling culture liquid for each microorganism culture apparatus is increased; (4) various microorganism culture apparatus can be used individually or be easily combined, so that energy is saved when single apparatus is used to conduct microorganism culturing; (5) simple and convenient operation, easy maintenance.

BRIEF DESCRIPTION OF THE DRAWINGS

Further description to this invention will be made in conjunction with accompanying drawings and specific embodiments. Identical or similar parts in the drawings will be denoted in identical reference signs.

FIG. 2A is a partial sectional view of the impeller. FIG. 2B is a section view along line 2B—2B of FIG. 2A.

DESCRIPTION OF THE PREFERRED EMBODIMENTS

Figure 1:
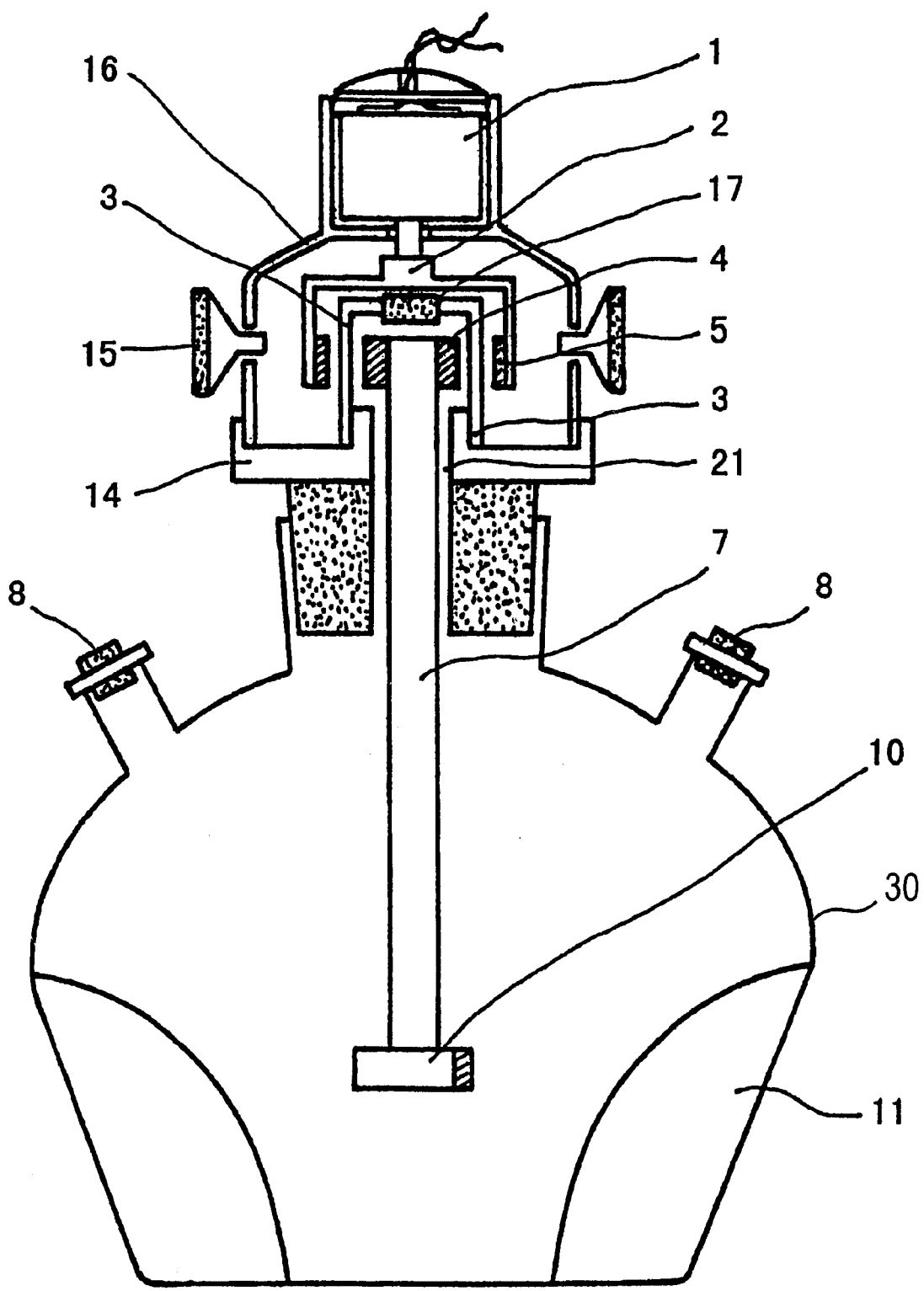
FIG. 1 is a cross-section of magnetically coupled microorganism culture apparatus according to one embodiment of this invention.

Referring to FIG. 1, it shows the magnetically coupled microorganism culture apparatus (culture flask) according to one embodiment of this invention. As shown in FIG. 1, this apparatus can be divided into fixed parts and rotary parts.

The fixed parts include a flask body 30; a plurality of outlets 8 and an opening (i.e. flask mouth) 21 arranged at the top of the flask body; an air-purifying chamber 16 fastened airtight to the flask opening; a plurality of gas inlets 15 on the wall of the air-purifying chamber; a sealed filtering cap 3 in the chamber covering hermetically said opening 21; and an inlet 17, other than which there is no gas exchange path between interior of the sealed cap and the rest of the chamber. Inlets 15, 17 and outlet 8 are all covered by air filtering films.

The rotary parts include a micro motor 1 on top of the air-purifying chamber; outer magnetic ring 5 on the inside wall of jacket 2 attached to the drive shaft of the micro motor; a hollow sucker 7 in the sealed cap, on the upper part of which is installed an inner magnetic ring 4. The outer and inner magnetic rings are located outside and inside of the sealed cap respectively. The sucker passes through opening 2 and enters into the flask.

When the power is on, micro motor 1 rotates at a high speed, and outer magnetic ring 5 rotates correspondingly. The magnetic field of the outer magnetic ring passes through filtering sealed cap 3, acting on inner magnetic ring 4. The inner magnetic ring and outer magnetic ring are preferably located so that the relative coupling surface of the two magnetic rings are substantially parallel to the longitudinal axis of the micro motor drive shaft. The radially parallel location of the magnetic rings provides greater coupling area between them. The magnetic rings are magnetically coupled so that a rotation of the outer magnetic ring induces a rotation of the inner magnetic ring, which in turn brings the sucker 7 to rotate at a high speed. Fixed at the lower end of the sucker 7 is a hollow air impeller 10, which extends under the liquid surface. During the course of its high-speed rotation, the impeller continuously generates a centrifugal force, which casts the filtered fresh air into the liquid culture medium for the growth of the microorganism. After exchanging with the liquid culture medium, exhaust will be discharged out of the flask via outlet 8.

The inlet filtering system of the culture flask consists of two-stage air filters. The first stage is the inlets 15, on each of which is covered with an air filtering film of 0.45 $\mu$m–1 $\mu$m aperture made of teflon material for filtering the incoming air which goes through the inlet 15. The air filtered through the first stage passes through air-purifying chamber 16, and then enters via second inlet 17 into sucker 7, and is finally cast into the liquid in the flask by the rotating impeller. Inlet 17 and outlets 8 are all covered with an air filtering film of 0.2 $\mu$m aperture made of teflon material to obstruct any outside germs from entering, thus ensuring that the air finally reaching the sucker 7 is very clean.

The sucker enters through the flask cover (i.e. opening 21). With the diameter of the flask opening bigger than that of the sucker, it is guaranteed that the sucker can rotate freely. Additionally, the thickness of the inner magnetic ring and the diameter of the sucker are chosen such that the inner magnetic ring cannot fall into the flask, thus the impeller can float in the liquid without ever touching the bottom of the flask.

To allow more air to enter into the liquid culture medium, a dispersing ring 20 is set on the inside wall the flask body around the air impeller. The structure of the dispersing ring is shown in FIG. 2. When the air impeller rotates, the air cast out through passages 18 directed by the paddles 19 (leaves) on the dispersing ring, and then enters into the liquid culture medium for the growth of microorganisms. An alternative to the dispersing ring is a wing structure 11 (FIG. 1) at the interior bottom of the flask. The function of the wing structure is to slow down liquid in the flask and prevent it from generating eddy flows, thus producing a sufficient speed difference between the liquid around the impeller and the impeller itself to enable sufficient air release when the impeller rotates.

Figure 2A:
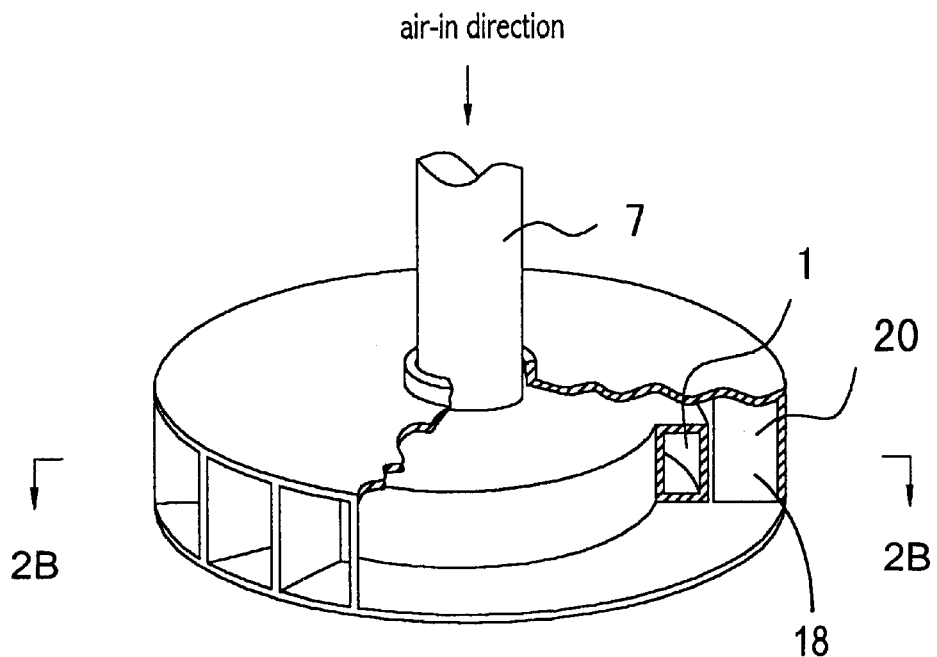
FIGS. 2A and 2B show the basic principle of a key element of said culture apparatus—impeller.
Figure 2B:
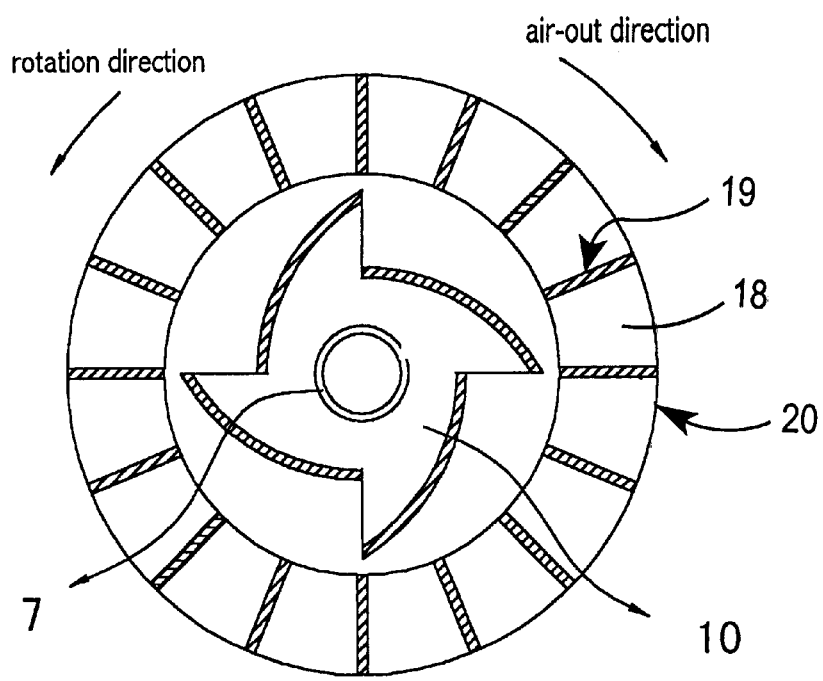

FIGS. 2A and 2B show a basic schematic diagram of one of the main parts of the culture apparatus, namely the air impeller, wherein FIG. 2A is a partial sectional view of the culture apparatus, and FIG. 2B is a sectional view thereof along line 2B—2B. The air impeller is a hollow impeller, with a gas outlet disposed at the end of each paddle of the impeller. The center of the impeller and the bottom of the sucker are communicated to each other. Therefore, when the impeller rotates in the liquid culture medium at a high speed, the air passes through the sucker, reaches the center of the impeller, and then enters axially into the paddle. When the impeller rotates counterclockwise, it casts the air into the liquid culture medium clockwise, thus providing enough fresh air for the growth of microorganisms. At the same time, a resulting increase of the air pressure in the culture flask causes the exhaust to be discharged from the outlet.

In this invention, impeller is preferably designed such that it is symmetrical relative to its rotating center to ensure smooth rotation.

Figure 3:
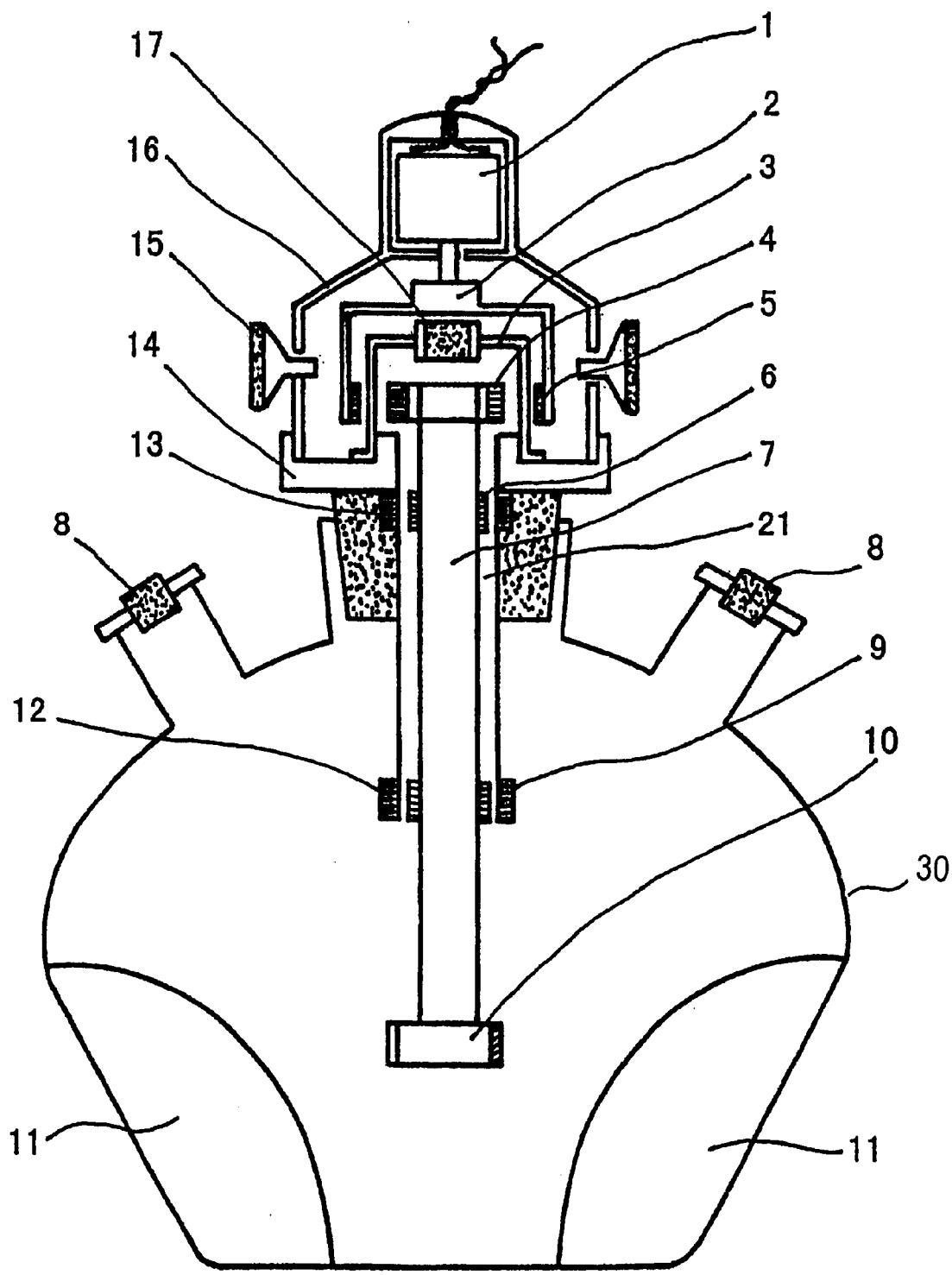
FIG. 3 is a cross-section of magnetically floating microorganism culture apparatus according to another embodiment.

FIG. 3 is an improvement of the culture medium described in FIG. 1. Besides the structure of FIG. 1, two pairs of balancing magnetic rings 6 (12), 9 (13) are positioned close to the middle of sucker 7. The exterior walls of inner magnetic rings 6,12 and the interior walls of outer magnetic rings 9,13 have identical polarities so that they repel each other. This is to ensure a steady position of the sucker's rotating shaft, i.e., the sucker always remains at a magnetic floating state relative to the flask mouth where it enters. With these additional magnetic rings, friction generated during the rotation of the sucker is minimized, so that the utilization of driving power is increased and the exchange of air is more efficient. The number of pairs of balancing magnetic ring may be one, two or more, provided that balance can be sufficiently maintained and the torque will not be increased excessively.

Figure 4:
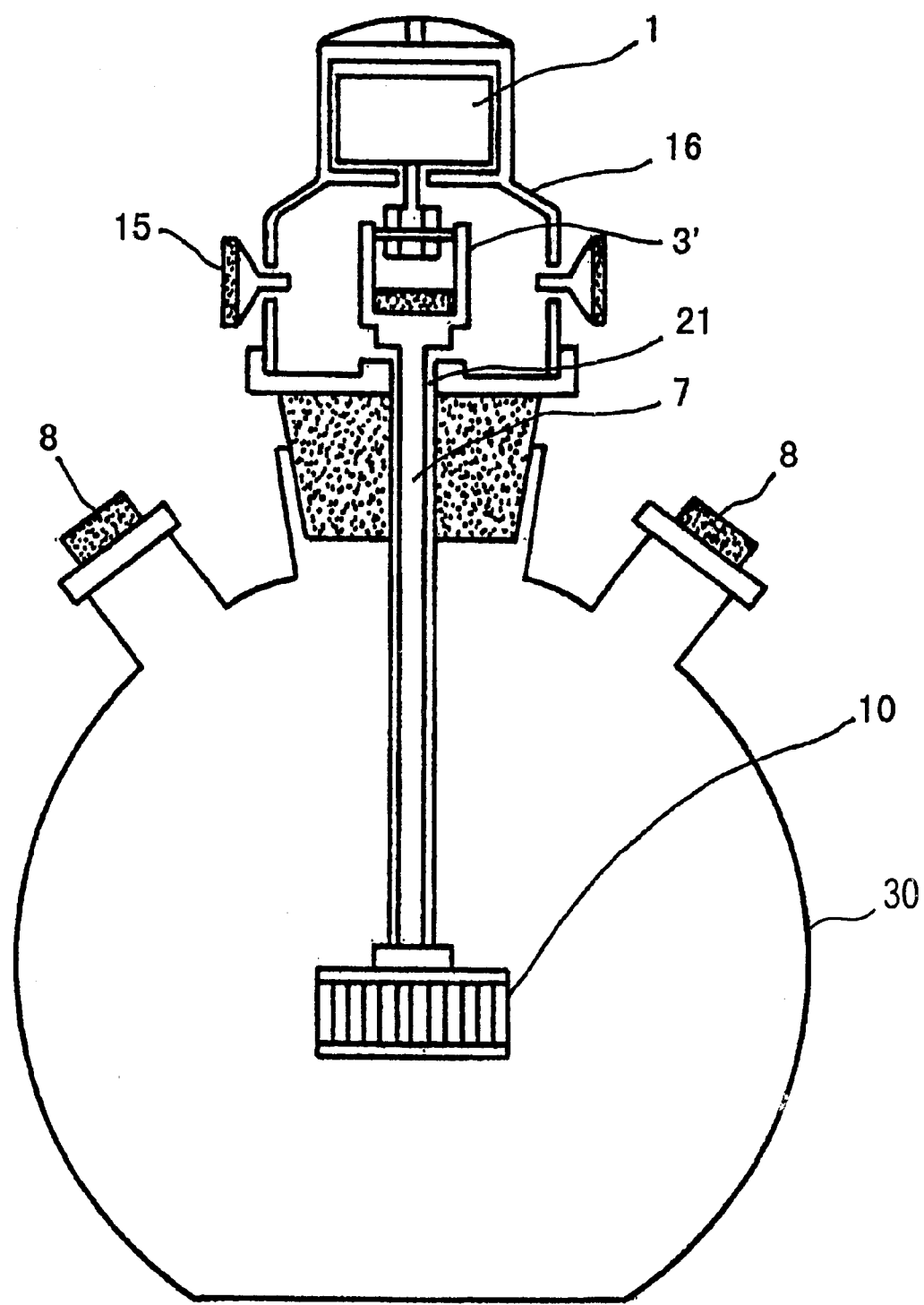
FIG. 4 is a cross-section of micro-power consumption microorganism culture apparatus according to another embodiment of this invention.

FIG. 4 is another variation of the culture apparatus shown in FIG. 1. Compared with the magnetically coupled apparatus of FIG. 1, this apparatus no longer uses magnetic driving power, but switches to a direct mechanical power generated by a micro motor disposed in the air-purifying chamber. In this embodiment, the sucker is mated fixedly to the driving shaft of the micro motor via shaft coupling 3', so that the central shaft of the sucker and the driving shaft of the micro motor share the same axial line. From the air-purifying chamber, air has to go through the filtering film disposed at the upper end of the sucker before entering the sucker. Thus, under the drive of the micro motor, the coupling pushes the sucker and further the impeller to rotate, casting the filtered fresh air into the liquid and realizing air exchange. This apparatus has advantages of a simple structure and a low cost. However, since the spacing between the shaft and sleeve is likely to be infected, the apparatus may not be kept aseptic for a long time.

Figure 5:
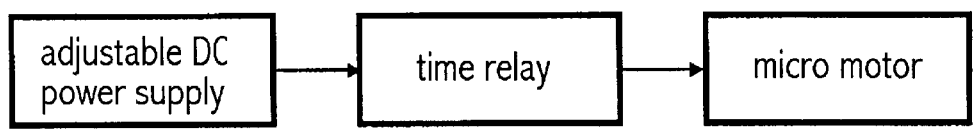
FIG. 5 is a control circuit possibly used in the culture apparatus shown in FIGS. 1, 3 and 4.

The culture apparatus as shown in FIGS. 1, 3, and 4 can work under the control of a time relay. When the power is on, the time relay generates a power signal with a certain duty cycle, which is output to the micro motor directly or after amplification by a power amplifier. When the power signal is on, the micro motor turns on and delivers oxygen of the air to the microorganism in the flask; when the power signal is off, the micro motor turns off, and oxygen delivery stops, thus controlling the rate of oxygen dissolution. A relevant control circuit is shown in FIG. 5. In fact, monolithic chip computer or other similar electronic devices can also be used instead of time relays, wherein a suitably programmed monolithic chip computer can achieve the same function as well.

Figure 6:
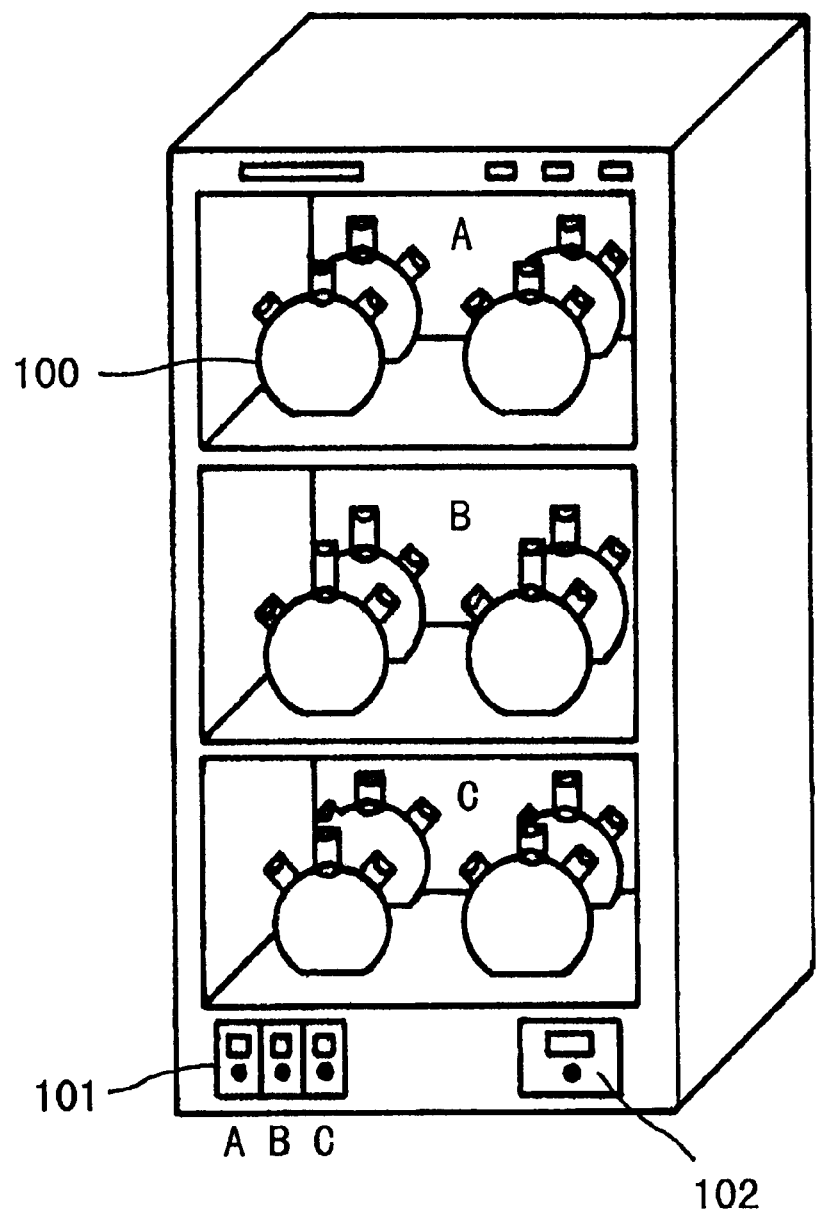
FIG. 6 is a microorganism culture system according to another embodiment of this invention.

FIG. 6 is a microorganism culture system according to this invention. This system includes a hexahedral box, wherein the front side of the box body is a transparent glass door. The inside of the box can be divided into several shelves, where microorganism culture apparatuses (magnetically coupled, magnetically floating or mechanically couples) can be placed on top. For easy illustration, a three-shelf box is assumed in the following example. Apparatuses on each shelf constitute a working area (A, B, C respectively). The on-offs of the micro motors on the culture flasks of each working area are controlled respectively by three time relays 101 (A, B, C) placed at the bottom of the box. Different on-off times may be set in different areas and they may be displayed on a panel at the same time. When the micro motor is turned on, oxygen is delivered to the microorganism in the flask of the apparatus, and when the motor is turned off, supply of oxygen is stopped, thus controlling the rate of oxygen dissolution. A temperature controller 102 may be built into the box body, thus maintaining the temperature in the box at a level most suitable for microorganism's growth. For example the temperature can be set to any level ranging 0 to 40° C., depending on the ideal culture environment of various microorganisms.

Figure 7:
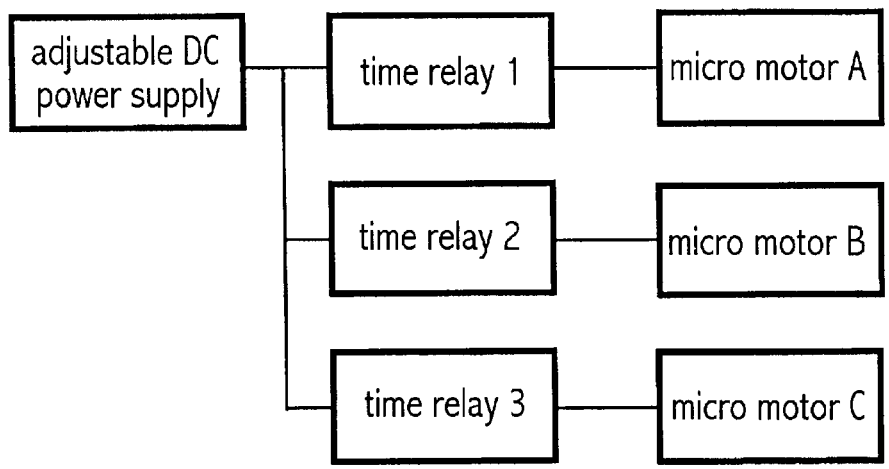
FIG. 7 is a schematic diagram of the system circuit used in FIG. 6.

FIG. 7 illustrates the circuit used by the microorganism culture system of FIG. 6. Commercial 220-V AC voltage is adapted, performed a full-wave current rectification, and then passed through a filtration network, thus generating 12-V DC power for the micro motor. The micro motors of the culture apparatuses in the three areas shown in FIG. 6 can be set to work under the control of respective time relays that are supplied by different adjustable DC powers. In addition, the time relays may be set to different duty cycles, i.e., different working durations, to control the on and/or off of the micro motors. The rotation speed of the micro motor is controlled by current output voltage, which is varied from 6 to 12V through the adjustment in potentiometer R. Different rotation speed of the micro motor changes the amount of the air entering into the flask. Equivalently, it changes the amount of oxygen dissolution. In this example, potentiometers can be replaced by other similar means, such as transformer tap, to adjust the voltage.

If the micro motor can be driven with alternating current, current rectification and filtration are no longer necessary, with the motor directly driven by AC signal.

The operation method of this invention is simpler than that of common flask shaker. First, remove the housing (FIG.

1-16) of the air-purifying chamber of each culture flask unit. Then, place said culture apparatus in a high-pressured sterilization cabin and sterilize it. Thirdly, after the culture medium cools down, vaccinate it. Finally, put the housing of the air-purifying chamber back on each apparatus (FIG. 1-14), turn on the power and it is ready to work.

The following is a result of the microorganism expansion culture by using the above said apparatus.

Example: Expansion culture for edible oyster cap fungus No.89

Liquid culture medium: corn starch 600 ml, malt juice 100 ml, bran 10 g.

Sterilization method: moist heat sterilization.

Sterilization requirement: 0.1 Mpa, 30 minutes.

Culture method: Pour liquid culture medium into an apparatus. Send it into a high-pressured sterilization cabin and sterilize it. When the culture medium cools to a temperature to about 30° C., vaccinate the fungus No.89 slant thallus to the liquid culture medium on a sterilized working table. The environmental temperature is controlled to 22° C.±1° C. for cultivation.

Culture time: 168 hours

Culture result:
1. Liquid thallus is 27 g/1000ml fermented liquid;
2. About 80% of thallus have a diameter less than 1.5 mm;
3. Thallus liquid has a special gardenia flavor, without abnormal flavor;
4. Fermented liquid pH value is about 5.6–5.8;
5. The oyster cap fungus growth from the liquid thallus is normal.

This invention can be widely used in fermentation engineering research, such as fermentation food, beverage, brewing, medicine, pesticide, enzyme, environmental protection, chemical mining, etc. It will also find wide application in the microbiological laboratories in universities and research institutes.

Although an explanation to some of the exemplary embodiments of this invention has been illustrated in conjunction with the figures, it should be understood that such embodiments are just for the purpose of explanation, not for the limitation of this invention. For example, instead of having filtering cap and the air-purifying chamber hermetically connected, they can be integrally made, thus hermetically cover the flask opening. As another example, in the above described embodiment, the impeller normally works under the liquid surface. However, when there is only a little liquid in the apparatus, the impeller rotates over the liquid surface, which also performs the function of air exchanger and help keep a normal growth of the microorganism. Therefore this invention will not be limited to the specific structure and arrangement as has been shown and described above. Apparently, those skilled in the art can make modifications and variations, without departing from the spirit and scope of this invention as will be described in the following claims.

What is claimed is:

1. A magnetically coupled microorganism culture apparatus, comprising:
   a container for holding microorganism culture medium liquid, said container having one or a plurality of gas outlets and an opening at a top of said container, each said outlet being covered by an air filtering film;
   a sealed filtering cap fixed over the container and covering said opening, said sealed cap having an inlet which is covered by an air filtering film;
   a hollow sucker placed through the sealed cap pointing downward into the container, which can rotate relative to the sealed cap and the container body;
   a hollow air impeller connected at a lower end of the sucker; which is in gaseous communication with said sucker;
   a driven magnet fastened to the upper end of the sucker;
   resisting structures fixed within the container near the impeller, for preventing the liquid in the container from generating an eddy flow; and
   two or more than two pairs of balancing inner magnetic rings and outer magnetic rings arranged close to a middle part of the sucker, wherein said inner magnetic rings are fastened to the outside wall of the sucker, and the outer magnetic rings are relatively fixed to the container, the outside walls of the inner magnetic rings and the inner wall of the outer magnetic rings have the same polarities and thus repel each other, thereby preventing the sucker from touching the container while rotating;
   when a rotary magnetic field is applied to said culture apparatus the driven magnet brings the sucker and then the impeller to rotate along with the driven magnet, thus sucking air which enters via the inlet and is filtered into the liquid by the centrifugal force so as to achieve an air exchange.

2. The microorganism culture apparatus according to claim 1, further comprising a micro motor, and a driving magnet fastened to a driving shaft of said micro motor, said driving magnet being disposed outside the sealed cap and magnetically coupled to the driven magnet, said rotary magnetic field being generated when the micro motor is turned on and the driving magnet rotates.

3. The microorganism culture apparatus according to claim 2, wherein the micro motor is supplied with a driving current of a certain duty cycle by a power supply and a time relay in connection with the micro motor, said duty cycle being controlled by the time relay.

4. The microorganism culture apparatus according to claim 3, wherein the voltage supplied to the micro motor is adjusted by a potentiometer or tapped transformer to between 6V and 12V so that the rotation speed of the micro motor is controlled and thus the oxygen dissolution rate.

5. The microorganism culture apparatus according to claim 2, wherein the micro motor is supplied with a driving current of a certain duty cycle, wherein the cycle is controlled by a preprogrammed monolithic chip computer.

6. A microorganism culture system using the microorganism culture apparatus according to claim 2, comprising a box body, an adjustable DC power supply, a plurality of microorganism culture apparatuses arranged in the box body, and several corresponding time relays, wherein each said microorganism culture apparatus is one according to claim 2; and said plurality of culture apparatuses are divided into several groups, with the time relay for controlling the micro motors of each group of the culture apparatuses having different duty cycles so that different amounts of oxygen may be delivered to different groups of said culture apparatuses, thus achieving the purpose of simultaneously cultivating different microorganisms in the same box body.

7. A system according to claim 6, wherein a temperature controller is provided for controlling the internal temperature within the box body so as to meet the temperature requirement for the microorganisms.

8. The microorganism culture apparatus according to claim 1, further comprising an alternating current electric micro motor, and a driving magnet fastened to a driving shaft of said micro motor, said driving magnet being disposed outside the sealed cap and magnetically coupled to the driven magnet, said rotary field being generated when the micro motor is supplied with an alternating current and the driving magnet rotates.

9. The microorganism culture apparatus according to claim 1, further comprising an air-purifying chamber positioned outside the sealed filtering cap, wherein one or a plurality of air inlets with air filtering films are provided on the air-purifying chamber, and wherein the air filtering films are used to enforce the filtration to the incoming air.

10. A microorganism culture apparatus, comprising:
   a container for holding microorganism culture medium liquid, said container including one or a plurality of gas outlets and an opening at a top of the container, each said outlet being covered by an air filtering film;
   an air-purifying chamber fixed over the container, the wall of said air-purifying chamber having one or a plurality of inlets which is/are covered by air filtering films;
   a hollow sucker in the air-purifying chamber, passing downward through the opening and entering into the container, an upper end of the sucker being fastened to the driving shaft of a micro motor via a coupling, an upper opening of the sucker being covered by air filtering film;
   an impeller fixed at a lower end of the sucker, said impeller being in a gaseous communication with said sucker;
   a resisting structure being fastened to the container near the impeller; for preventing the liquid in the container from generating an eddy flow; and
   two or more than two pairs of balancing inner magnetic rings and outer magnetic rings arranged close to the middle part of the sucker, wherein said inner magnetic rings are fastened to the outside wall of the sucker, and the outer magnetic rings are relatively fixed to the container, the outside wall of the inner magnetic rings and the inner wall of the outer magnetic rings have the same polarities and thus repel each other, thereby preventing the sucker from touching the container while rotating;
   wherein the sucker is the only gaseous passage between the air-purifying chamber and the container;
   when the micro motor is switched on, the micro motor drives the sucker and the impeller to rotate, thus sucking filtered air which enters into the sucker via the inlet into the liquid by the centrifugal force and achieving the goal of air exchange between the inside and outside of the container.

11. A method for conducting aseptic air exchange for the microorganism in a container by means of magnetic coupling, said container including a container body for holding microorganism culture medium liquid, said container body including one or a plurality of outlets and an opening at a top of the container, each said outlet being covered by an air filtering film; a resisting structure located at the bottom of and fastened relative to the container, for preventing the liquid in the container from generating an eddy flow when rotating;
   said magnetically coupled rotary means including a sealed filtering cap, on which is provided an inlet having an air filtering film; a hollow sucker within the sealed cap which is movable relative to the sealed cap; an impeller fastened at the bottom of the sucker, said impeller being in a gaseous communication with the sucker; a driven magnet fastened at the top of the sucker; and two or more than two pairs of balancing inner magnetic rings and outer magnetic rings arranged close to the middle part of the sucker, wherein said inner magnetic rings are fastened to the outside wall of the sucker, and the outer magnetic rings are relatively fixed to the container, the outside wall of the inner magnetic rings and the inner wall of the outer magnetic rings have the same polarities and thus repel each other, thereby preventing the sucker from touching the container while rotating;
   said method including the following steps:
      lowering the sucker together with the impeller into the container through the container's sealing cover so that the impeller is at the same level as said resisting structure;
      fastening the sealed filtering cap onto and covering the opening of the container, so that air flow between the sealed cap and the container is only allowed through the sucker;
      applying a rotary magnetic field to the driven magnet;
      the driven magnet bringing the sucker and further the impeller to rotate;
      the filtered air, which enters into the sucker via the inlet, being sucked into the liquid by the centrifugal force so as to achieve air exchange.

* * * * *